United States Patent
Hastenteufel et al.

(10) Patent No.: US 9,364,686 B2
(45) Date of Patent: Jun. 14, 2016

(54) PLANNING A TREATMENT BEAM AIMED AT ONE OR MORE TARGET REGIONS

(71) Applicants: Mark Hastenteufel, Heidelberg (DE); Markus Stoll, Heidelberg (DE)

(72) Inventors: Mark Hastenteufel, Heidelberg (DE); Markus Stoll, Heidelberg (DE)

(73) Assignee: Siemens Aktiengesellschaft, München (DE)

( * ) Notice: Subject to any disclaimer, the term of this patent is extended or adjusted under 35 U.S.C. 154(b) by 43 days.

(21) Appl. No.: 14/200,008

(22) Filed: Mar. 6, 2014

(65) Prior Publication Data
US 2014/0257012 A1   Sep. 11, 2014

(30) Foreign Application Priority Data
Mar. 7, 2013  (DE) .......................... 10 2013 203 917

(51) Int. Cl.
*A61N 5/10*  (2006.01)
(52) U.S. Cl.
CPC .................................. *A61N 5/1031* (2013.01)
(58) Field of Classification Search
CPC ................................................... A61N 5/1031
See application file for complete search history.

(56) References Cited

U.S. PATENT DOCUMENTS

| 7,369,645 B2 * | 5/2008 | Lane ................................ 378/65 |
| 7,831,289 B2 * | 11/2010 | Riker et al. .................... 600/407 |
| 7,978,817 B2 | 7/2011 | Rietzel |
| 2010/0086183 A1 * | 4/2010 | Vik et al. ....................... 382/128 |
| 2012/0310615 A1 * | 12/2012 | Moore ................ G06F 19/3437 703/11 |
| 2013/0079579 A1 * | 3/2013 | Hastenteufel ............ A61N 5/10 600/1 |

FOREIGN PATENT DOCUMENTS

| DE | 102008019128 | 10/2009 |
| DE | 102011075738 | 11/2012 |
| DE | 102011075738 A1 * | 11/2012 |
| DE | 102011083414 | 3/2013 |

OTHER PUBLICATIONS

Andrezej Niemierko et al., "Calculation of Normal Tissue Complication Probability and Dose-Volume Histogram Reduction Schemes for Tissues with a Critical Element Architecture", Radiotherapy and Oncology, 1991, pp. 166-176, vol. 20, Elsevier.
D. Maleike et al., "Simulation and Visualization of Dose Uncertainties Due to Interfractional Organ Motion", Physics in Medicine and Biology, Apr. 19, 2006, pp. 2237-2252, vol. 51, Institute of Physics Publishing.
German Office Action dated Feb. 10, 2014 in corresponding German Patent Application No. DE 10 2013 203 917.4 with English translation.

(Continued)

*Primary Examiner* — Jack Berman
(74) *Attorney, Agent, or Firm* — Lempia Summerfield Katz LLC

(57) ABSTRACT

A method and an apparatus for planning a treatment beam aimed at at least one target region are provided. Planning parameters having associated predetermined parameter values are for performing a treatment that is to be applied with the treatment beam. The method includes defining a first predetermined parameter value of the planning parameters that is suitable for the irradiation of a treatment region that includes at least one target region. The method also includes ascertaining, based on the first predetermined parameter value, a first probability distribution in relation to an optimizable variable that is prespecified based on deviations to be expected when carrying out the irradiation.

13 Claims, 4 Drawing Sheets

(56) References Cited

OTHER PUBLICATIONS

Jan Unkelbach et al., "Reducing the Sensitivity of IMPT Treatment Plans to Setup Errors and Range Uncertainties via Probabilistic Treatment Planning", Med. Phys., Jan. 2009, pp. 149-163, vol. 36, No. 1, Am. Assoc. Phys Med.

Markus Stoll et al., "Transfer of Methods from Radiotherapy Planning to Ablation Planning with Focus on Uncertainties and Robustness", Biomed Tech., 2012; 57 (Suppl. 1), 2012, 4 pages.

Panayiotis Mavroidis et al., "Response-Probability Volume Histograms and ISO-Probability of Response Charts in Treatment Plan Evaluation", Med. Phys., May 2011, pp. 2382-2397, vol. 38, No. 5, Am. Assoc. Phys. Med.

Wei Chen et al., "Including Robustness in Multi-Criteria Optimization for Intensity-Modulated Proton Therapy", Physics in Medicine and Biology, 2012, pp. 591-608, vol. 57, IOP Publishing.

Wei Liu et al., "Robust Optimization of Intensity Modulated Proton Therapy", Med. Phys., Feb. 2012, pp. 1079-1091, vol. 39, No. 2, Am. Assoc. Phys. Med.

\* cited by examiner

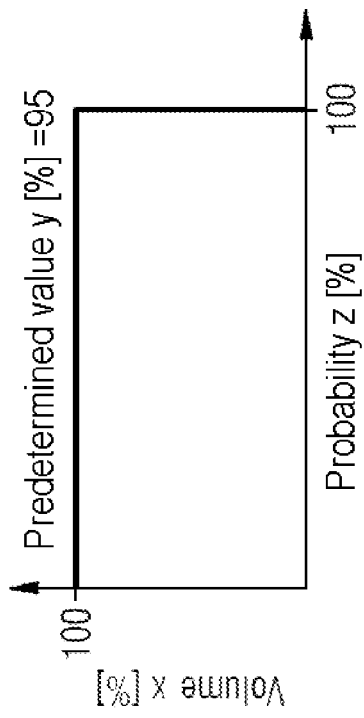
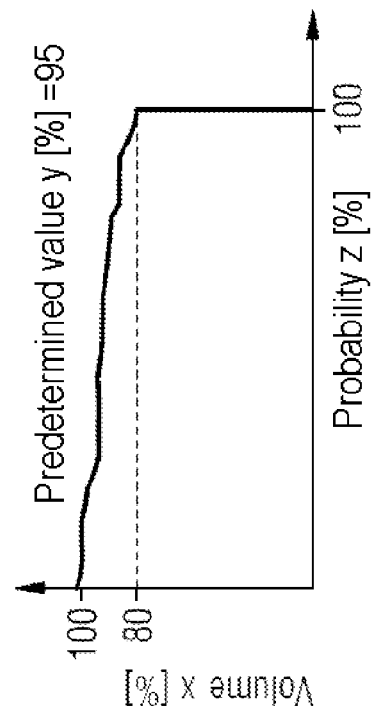
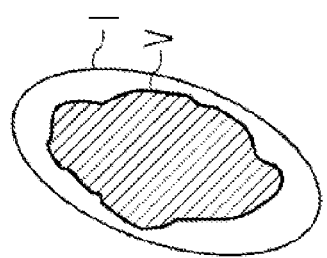
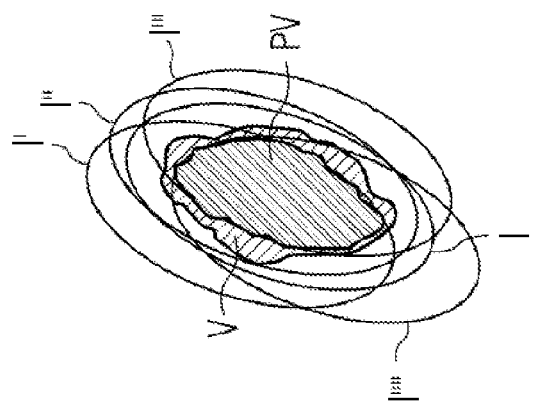

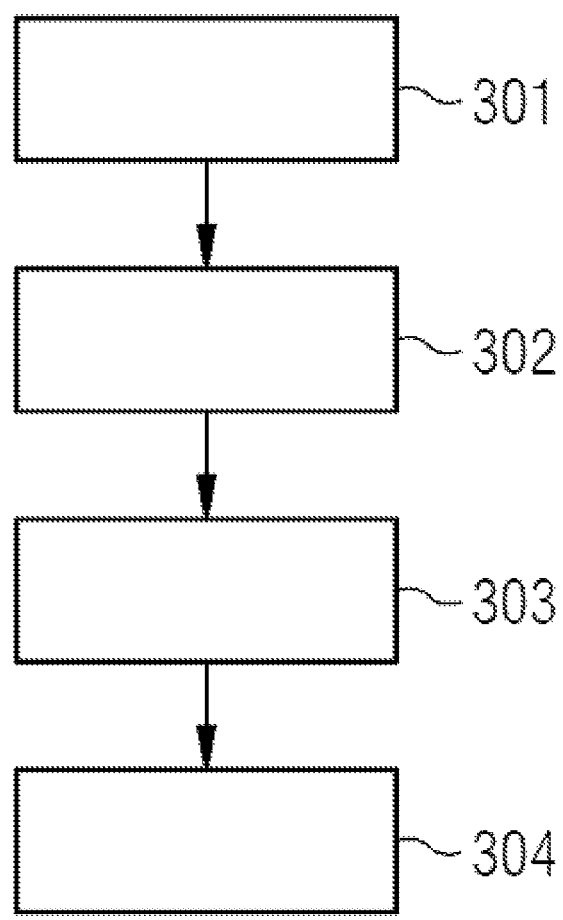

PLANNING A TREATMENT BEAM AIMED AT ONE OR MORE TARGET REGIONS

This application claims the benefit of DE 10 2013 203 917.4 filed on Mar. 7, 2013, which is hereby incorporated by reference in its entirety.

BACKGROUND

The present embodiments relate to an apparatus and a method for planning a treatment beam aimed at one or more target regions.

In addition to beam therapy, chemotherapy and surgical removal, ablation has developed into an increasingly important minimal-invasion method in oncology, allowing the complete removal of tumors and thus the prevention of any further spread of the pathological tissue.

DE 10 2011 075 738 A1 discloses a method and an apparatus for ascertaining a robust ablation program for ablation of a tissue region. The program includes one or more ablation parameters that define the performance of the ablation and have associated predetermined parameter values. Based on first probability distributions for first predetermined parameter values, a second probability distribution of expected second ablation regions is ascertained. Second predetermined parameter values of the ablation parameters are chosen such that a third ablation region is ablatable. The third ablation region is ascertained from the second probability distribution and the expected second ablation regions with the optimization or maximization of at least one prespecified variable.

In beam therapy, X-rays, electron beams, laser beams or particle beams irradiate diseased tissue, among others. In recent years, particle therapy, for example, has become an established method for treating tissue (e.g., tumors), although irradiation methods, as are used as part of particle therapy, may also be employed in non-therapeutic areas such as, for example, the irradiation of phantoms or non-living bodies for research, in the irradiation of materials, etc.

In particle therapy, particles are generated (e.g., ions such as protons, carbon ions or other ion types). The particles are accelerated to high energies in an accelerator, shaped to form a particle beam, and subsequently aimed at the tissue to be irradiated. The particles penetrate the tissue to be irradiated and release energy in a circumscribed area. The depth of penetration of the particle beam into the tissue to be irradiated is primarily dependent on the energy of the particle beam. The higher the energy of the particle beam, the deeper the penetration of the particles into the tissue to be irradiated.

The total amount of radiation to be delivered by the irradiation apparatus is to be determined during the beam therapy planning process.

In beam therapy, the beam therapy plan is calculated and may be displayed on a display/monitor, without taking an uncertainty into consideration. Such uncertainty may result, for example, from errors/variations in the Hounsfield units, from adjustment errors or from contour errors/contour changes.

Hounsfield variations may result from a changed anatomy of the patient, while Hounsfield errors occur as a result of inaccuracies during image capturing or reconstruction. Contour changes may result from the tumor being located at an unexpected location, while contour errors occur if the tumor has not been correctly plotted.

In order to incorporate such uncertainty in the planning process of the beam therapy, the robustness of the planning is evaluated. It is the aim of a radiation therapy plan to determine the ideal radiation dose (e.g., distribution) under the aspect of having as great a robustness as possible. The parameters radiation dose and robustness are weighed against each other.

The following radiation dose planning methods are known: 1. a representation of a color-coded probability when an image voxel reaches or exceeds a certain dose (e.g., see "Simulation and visualization of dose uncertainties due to interfractional organ motion," Phys. Med. Biol. 2006, pages 2237-2252); and 2. a series of dose-volume curves (e.g., see Wei Chen et al., "Including robustness in multi-criteria optimization for intensity-modulated proton therapy," Phys. Med. Biol. 57, IOP publishing, pages 591-608; Wei Liu et al., "Robust optimization of intensity modulated proton therapy," Medical Physics, vol. 39, no. 2, Am. Assoc. Phys. Med., pages 1079-1091; and Jan Unkelbach et al., "Reducing the sensitivity of IMPT treatment plans to set up errors and range uncertainties via probabilistic treatment planning," Med. Phys. 36 (1), Am. Assoc. Phys. Med., pages 149-163).

SUMMARY AND DESCRIPTION

The scope of the present invention is defined solely by the appended claims and is not affected to any degree by the statements within this summary.

The present embodiments may obviate one or more of the drawbacks or limitations in the related art. For example, an apparatus and a method for carrying out an irradiation treatment with a treatment beam, where minimized radiation dose is achieved together with maximized robustness, are provided.

One aspect is a method for planning a treatment beam aimed at at least one target region (PV). The method includes planning parameters, having associated predetermined parameter values, for performing a treatment that is to be applied with the treatment beam. The method includes defining a first predetermined parameter value of the planning parameters that is suitable for the irradiation of the treatment region. The treatment region includes at least one target region. Based on the first predetermined parameter value, a first probability distribution is ascertained in relation to an optimizable variable that is prespecified based on the deviations to be expected when carrying out the irradiation.

A further, second predetermined parameter value may be determined with optimization or maximization (304) of the optimizable variable and of the first probability distribution. Based on the second predetermined parameter value, a second probability distribution may be ascertained.

The above-mentioned method acts are repeatable.

The first predetermined parameter value may express a value with as close a match as possible between an isoline or isoarea that is adaptable for controlling the dose of the treatment beam, and a contour defining the treatment region.

The optimizable variable may represent a volume portion of the treatment region. The volume portion is treatable with a probability from the first probability distribution in relation to the predetermined parameter value.

The second predetermined parameter value or a plurality of further predetermined parameter values may represent a duration of the irradiation using the treatment beam and/or an angle of incidence of the treatment beam.

According to one or more of the present embodiments, a measure of robustness is introduced into the therapy planning. Robustness measures are shown together with the known dose-volume histogram (DVH). This produces a probability-volume histogram (PVH), which, in terms of the type of representation, is similar to the dose-volume histogram mentioned above. Accordingly, the user of the therapy planning may quickly become accustomed to the representation according to the present embodiments.

One further development provides for the radiation dose to be within one or more limit values.

One further development provides for the limit value or limit values of the radiation dose to be pre-set or set automatically or manually via a user interface.

A further aspect is an apparatus for controlling a treatment beam aimed at an object. The apparatus includes devices (e.g., one or more processors) or modules for carrying out the above-mentioned method. The devices or modules may in each case be realized in terms of hardware, firmware, and/or software or as a computer program on a non-transitory computer readable medium.

The apparatus may be implemented in a control or regulation unit, a computer or a server.

The at least one set of image data and the isoline or isoarea may be visually represented on a display apparatus. Settings may be changed via a user interface (e.g., a mouse, keyboard, touch screen etc.).

The apparatus or the computer program may be configured or implemented correspondingly, like the method.

BRIEF DESCRIPTION

FIG. 3 shows an exemplary target region to be irradiated, which is enclosed by an isoline;

FIG. 4 shows exemplary target regions, where various target regions are enclosed by various isolines that occur on account of errors;

FIG. 5 shows a flowchart of a method according to one or more of the present embodiments;

FIG. 6 shows an exemplary probability-volume histogram without uncertainty; and

FIG. 7 shows an exemplary probability-volume histogram with an uncertainty.

DETAILED DESCRIPTION

Figure 1:
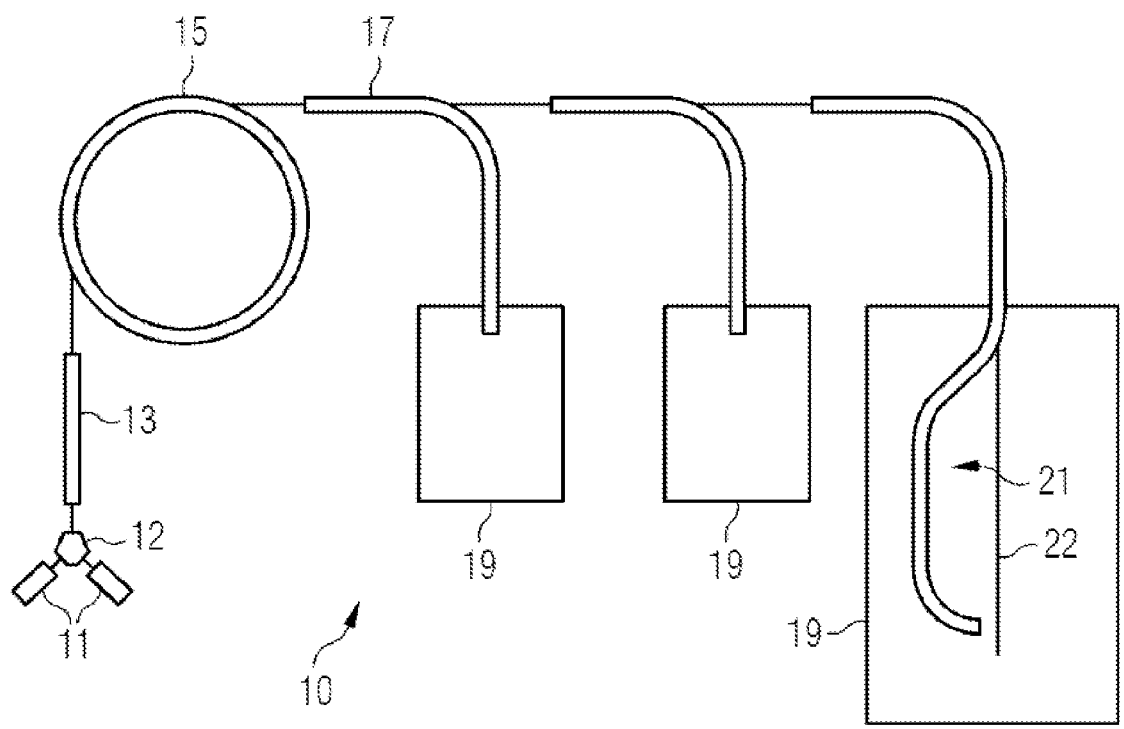
FIG. 1 shows a particle therapy system.
Figure 2:
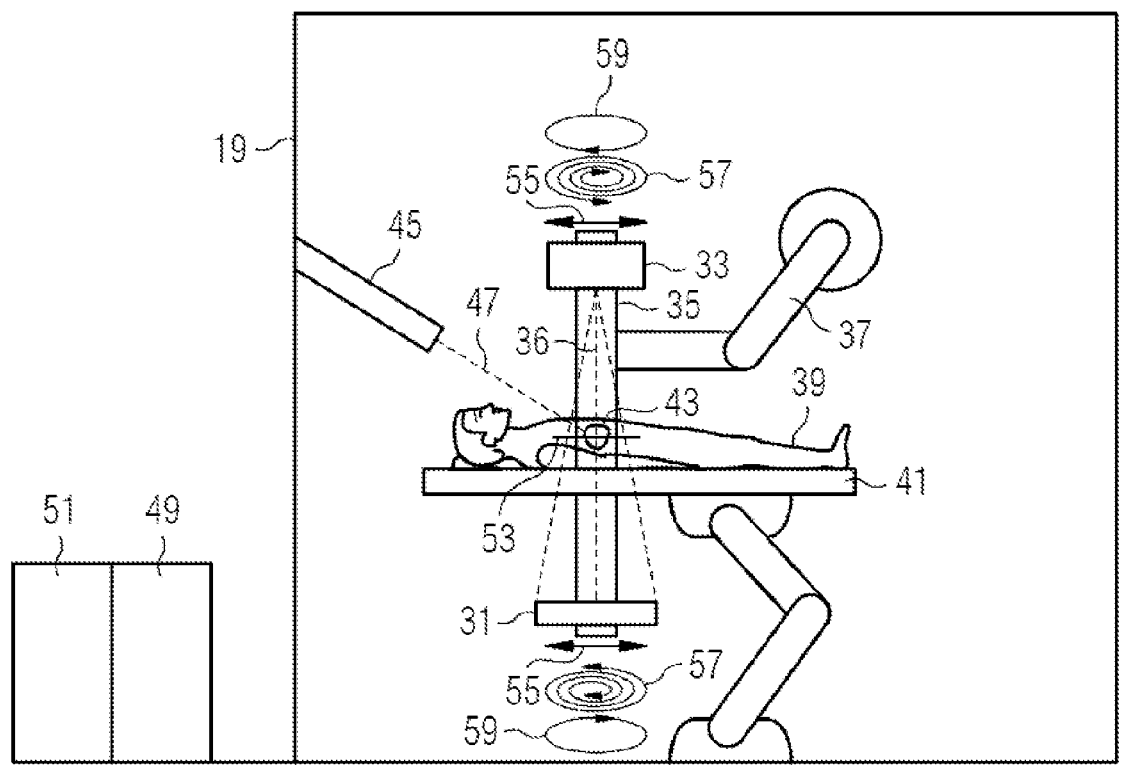
FIG. 2 shows an arrangement of a beam output and an imaging unit in an irradiation room.

FIGS. 1 and 2 schematically illustrate a particle therapy system and an arrangement of a beam output and of an imaging unit, as are already known for example from DE 10 2008 019 128 A1.

FIG. 1 shows a schematic overview of the construction of a particle therapy system 10. In a particle therapy system 10, a body (e.g., a tissue with a tumor) is, for example, irradiated with a particle beam.

Particles used may be ions such as, for example, protons, pions, helium ions, carbon ions or other ion types. Such particles may be generated in a particle source 11. If, as illustrated in FIG. 1, two particle sources 11 that generate two different types of ions are present, these two types of ions may be switched between within a short time interval. For example, a switching magnet 12 that is arranged between the ion sources 11 on the one side and a pre-accelerator 13 on the other side is used. It is thus, for example, possible for the particle therapy system 10 to be operated with protons and carbon ions at the same time.

The ions that are generated by the ion source 11 or one of the ion sources 11 and, if appropriate, selected using the switching magnet 12, are accelerated in the pre-accelerator 13 to a first energy level. The pre-accelerator 13 is, for example, a linear accelerator (LINAC, "linear accelerator"). The particles are subsequently fed into an accelerator 15 (e.g., a synchrotron or a cyclotron). The particles are accelerated in the accelerator 15 to high energies as are necessary for irradiation. Once the particles leave the accelerator 15, a high-energy beam transport system 17 guides the particle beam to one or more irradiation rooms 19. Inside an irradiation room 19, the accelerated particles are aimed onto a body to be irradiated. Depending on the configuration, this takes place from a fixed direction (e.g., in "fixed beam" rooms) or from different directions by a rotatable gantry 21 that is movable about an axis 22.

The construction of a particle therapy system 10, illustrated by way of FIG. 1, may be for many particle therapy systems, but may also deviate from this. The exemplary embodiments described below are employable both in conjunction with the particle therapy system illustrated by way of FIG. 1 and with other particle therapy systems.

FIG. 2 shows a possible arrangement of a beam output and the imaging unit in an irradiation room.

The imaging unit includes an x-ray detector 31 and an x-ray emitter 33. The x-ray detector 31 and the x-ray emitter 33 are arranged opposite one another on a carrier arm 35 (e.g., a C-arm). The carrier arm 35 is positionable flexibly in the room using a robot arm 37 (e.g., using a six-axis jointed-arm robot). The x-ray detector 31 and the x-ray emitter 33 may be used to take x-ray recordings (e.g., transillumination recordings) of a patient 39 who is positioned on a patient bed 41 for irradiation. For example, the target region to be irradiated or the target volume 43 to be irradiated (e.g., an organ to be irradiated) that is afflicted with a tumor may be imaged in the transillumination recordings.

As an alternative to the embodiment using the carrier arm, the x-ray detector and the x-ray emitter may be positioned independently from one another (e.g., via two robot arms). This may allow increased flexibility, since no rigid carrier arm is arranged between the x-ray emitter and the x-ray detector.

In one embodiment, only one of the x-ray detector and the x-ray emitter may be positioned such that the x-ray detector or the x-ray emitter is movable. Only the other of the x-ray detector and the x-ray emitter may be positioned statically. For example, the x-ray detector may move, and a movable stop on the x-ray emitter may provide that the x-rays are allowed to variably pass.

For irradiation, a particle beam 47 exits a beam output 45 and is aimed onto the patient 39. A beam output 45 that is spatially fixedly installed in the room is shown. Alternatively, the beam output 45 may be attached to a rotatable gantry, such that the beam output 45 may be rotated about the patient 39. However, during the application of the particle beam 47, the beam output 45 may remain stationary.

The positioning of the x-ray detector 31 and of the x-ray emitter 33 may take place independently of the beam output 45. During the application of the particle beam 47, the carrier arm 35 is moved back and forth by the robot arm 37. In the course of this, a series of transillumination images is recorded. From the series of transillumination images, a series of digital tomosynthesis images are reconstructed "online". In other words, the series of digital tomosynthesis images are reconstructed during the application of the particle beam 47 (e.g., "on-the-fly" reconstruction). The recorded transillumination images are transmitted to a computer unit 49, in which the tomosynthesis images are reconstructed.

In the series of digital tomosynthesis images, the movement of the target volume 43 (e.g., during the application of the particle beam 47) may be evaluated. This evaluation takes place "on the fly." The information obtained in this manner is used to control or regulate the profile of the irradiation and the radiation dose. Evaluation and control of the profile of the irradiation and of the radiation dose take place in a control unit 51. For example, the particle beam 47 may be switched off as soon as the target volume 43 to be irradiated is no longer in a desired position, and may be switched on again as soon as the target volume 43 to be irradiated is once again in the desired position. Alternatively and/or additionally, the particle beam 47 may track a movement of the target volume 43 if the movement of the target volume 43 takes place within specific limits.

The control unit 51 and/or the computer unit 49 for image reconstruction may be implemented in a single computer unit or may be split up in different subunits that are implemented as separate units. Alternatively, the control unit 51 and/or the computer unit 49 may be implemented in a control unit for the entire particle therapy system.

The carrier arm 35 may be moved in various ways. A simple movement is indicated by a double-headed arrow 55 and corresponds to a pivot movement. Another option for moving the carrier arm 35 is a circular or helical movement, indicated by the spiral 57 or the circle 59. In the latter two movements, the x-ray axis 36 performs a precision movement.

FIG. 3 shows a target region or a target volume V and an isoline or an isoarea I. The isoline I of the radiation dose may be altered using a user operating element, as already suggested, for example, in DE 102011083414.1. Such changes may be visualized in real time. The isoline is determined such that the isoline matches the contour of the target region as well as possible.

FIG. 3 shows a schematic illustration of an exemplary first target region V that is intended to be irradiated, as is produced, without the inclusion of errors in the implementation of a therapy plan. It is assumed that the target region V is enclosed completely by the isoline I to a predetermined (parameter) value of 95% of the radiation dose. The target region indicates the tissue region in which on account of irradiation for a predetermined period of time, the tumor cells are destroyed completely. The shape of the target region is not to scale. In reality, the target region resembles more a spherical shape. However, features and characteristics of the tissue to be treated, such as, for example, the type of tissue, any blood vessels that may be present, etc., are not taken into account. A more accurate ascertainment of the target region in dependence on the radiation dose and duration may be provided based on physics models that simulate the irradiation process. The tissue properties are taken into account. In this respect, FIG. 3 shows a situation, in which therapy planning is implemented without errors, and the resulting first target region V was ascertained close to reality. However, this scenario does not correspond to the reality or to practice. In reality, therapy planning, in which exact first predetermined parameter values are prespecified for corresponding therapy parameters, is not implemented in an ideal fashion. In this context, FIG. 4 shows examples that will be explained below.

FIG. 4 shows a schematic illustration of three further exemplary isolines I', I'', I''', I'''', where the isolines I', I'', I''', I'''' enclose a second target region PV, and where the target region PV encloses a volume x of 80% of the first target region V with a probability z<=100%. PV is enclosed by an intersection of a plurality of such isolines (e.g., I', I'', I''', I'''').

FIG. 6 shows an exemplary probability-volume histogram (PVH) of the situation illustrated in FIG. 3, in which the X axis indicates the probability, and the Y axis indicates the volume of the target region V in percent.

FIG. 7 shows an exemplary probability-volume histogram (PVH) of the situation illustrated in FIG. 4, in which the X axis indicates the probability, and the Y axis indicates the volume of the target region V in percent.

The display or representation of the planning robustness according to one or more of the present embodiments of a radiation therapy plan will be explained below.

The following assumptions may be involved. a) Clinical staff are often interested only in a target region that allows a certain radiation dose (e.g., enclosed to 95% by an isoline). b) There are methods for determining a probability with which a particular percentage of a target region is enclosed by the isoline. By way of example, this may be carried out by "brute force" calculation, in which various radiation dose distributions are ascertained with various statistical uncertainties.

Accordingly, a probability-volume histogram (PVH), in which a target region (e.g., volume) of x % may yield a radiation dose of at least y % with a probability of z %, may be displayed. y is a first predetermined parameter (e.g., a prespecified height or a variable of radiation dose).

FIG. 5 illustrates a schematic flow chart of one embodiment of a method. In act 301, a first predetermined parameter value (e.g., y) of the radiation dose is chosen or defined such that a first target region V that encloses the tissue region or treatment region is treatable using the irradiation. In act 302, a first probability distribution (e.g., z %) of an expected second target region PV that encloses a volume portion (e.g., x %) of the first target region or treatment region V on account of the expected deviations when carrying out the irradiation, is ascertained based on the first predetermined parameter values. In act 303, a further, second predetermined parameter value (e.g., an irradiation duration) may be chosen or defined. This is defined in a method act 304 with optimization or maximization of an optimizable variable (e.g., the volume portion x and the first probability distribution z).

The method may be applied similarly with further predetermined parameter values (e.g., one or more angles of incidence of the irradiation beam in the target region (PV)) and further probability distributions.

When choosing the further predetermined parameter values (e.g., the duration of the irradiation or the angle of incidence), the further predetermined parameter values may be chosen such that as high a volume portion as possible (act 304) of the treatment region V is treatable with as high a probability as possible (e.g., in the case of a tumor, that the tumor is to be destroyed, if possible, completely).

The method according to one or more of the present embodiments allows the establishment of robust (e.g., error-tolerant) therapy planning programs. This makes possible better treatment successes. Further, the therapy planning programs may be used to reduce the precision requirements for the alignment or dose of the treatment beam.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for treatment with a treatment particle beam aimed at at least one target region, planning parameters having associated predetermined parameter values and being for performing the treatment that is to be applied with the treatment particle beam, the method comprising:
    defining a first predetermined parameter value of the planning parameters, the first predetermined parameter value being for an irradiation of the at least one treatment region, the at least one treatment region comprising at least one target region;
    ascertaining, based on the first predetermined parameter value, a first probability distribution defining a probability with which a volume portion of the treatment region is enclosed by an isoline or an isoarea, the volume portion being prespecified based on deviations to be expected when carrying out the irradiation; and
    performing, by a therapy system, the treatment based on at least one of the predetermined parameter values,
    wherein the at least one predetermined parameter value is controlled in accordance with the first probability distribution so as to control a dose of the treatment particle beam, to form an isoline or isoarea that defines a contour that is a close match with the prespecified volume portion of the treatment region.

2. The method of claim 1, further comprising determining a second predetermined parameter value with optimization or maximization of the optimizable variable and of the first probability distribution.

3. The method of claim 2, further comprising ascertaining, based on the second predetermined parameter value, a second probability distribution.

4. The method of claim 1, further comprising repeating the defining and the ascertaining.

5. The method of claim 2, wherein the second predetermined parameter value or a plurality of further predetermined parameter values represent a duration of the irradiation using the treatment particle beam, an angle of incidence of the treatment particle beam, or the duration of the irradiation using the treatment particle beam and the angle of incidence of the treatment particle beam.

6. The method of claim 1, wherein the dose of the treatment particle beam is within one or more limit values.

7. An apparatus for treatment with a treatment particle beam aimed at at least one target region, planning parameters having associated predetermined parameter values being for performing the treatment that is to be applied with the treatment particle beam, the apparatus comprising:
    a processor configured to:
    determine a first predetermined parameter value of the planning parameters, the first predetermined parameter value being for irradiation of a treatment region that comprises at least one target region; and
    ascertain a first probability distribution defining a probability with which a volume portion of the treatment region is enclosed by an isoline or an isoarea, the volume portion being prespecified based on deviations to be expected when carrying out the irradiation; and
    a therapy system configured to perform the treatment based on the first predetermined parameter value,
    wherein the first predetermined parameter value is controlled by said processor in accordance with the first probability distribution so as to control a dose of the treatment particle beam to form an isoline or isoarea that defines a contour that is a close match with the prespecified volume portion of the treatment region.

8. The apparatus of claim 7, wherein a second predetermined parameter value is determinable with optimization or maximization of the optimizable variable and of the first probability distribution.

9. The apparatus of claim 8, wherein the second predetermined parameter value or a plurality of further predetermined parameter values represent a duration of the irradiation using the treatment particle beam, an angle of incidence of the treatment particle beam, or the duration of the irradiation using the treatment particle beam and the angle of incidence of the treatment particle beam.

10. In a non-transitory computer-readable storage medium having a program code executable on a computer or in an integrated circuit to plan a treatment with a treatment particle beam aimed at at least one target region, planning parameters having associated predetermined parameter values and being for performing the treatment that is to be applied with the treatment particle beam, the program code comprising instructions, the instructions comprising:
    defining a first predetermined parameter value of the planning parameters, the first predetermined parameter value being for an irradiation of the at least one treatment region, the at least one treatment region comprising at least one target region;
    ascertaining, based on the first predetermined parameter value, a first probability distribution defining a probability with which a volume portion of the treatment region is enclosed by an isoline or an isoarea, the volume portion being prespecified based on deviations to be expected when carrying out the irradiation; and
    performing, by a therapy system, the treatment based on at least one of the predetermined parameter values,
    wherein the at least one predetermined parameter value is controlled in accordance with the first probability distribution so as to control a dose of the treatment particle beam to form an isoline or isoarea that defines a contour that is a close match with the prespecified volume portion of the treatment region.

11. The non-transitory computer-readable storage medium of claim 10, wherein the instructions further comprise determining a second predetermined parameter value with optimization or maximization of the optimizable variable and of the first probability distribution.

12. The non-transitory computer-readable storage medium of claim 11, wherein the instructions further comprise ascertaining, based on the second predetermined parameter value, a second probability distribution.

13. The non-transitory computer-readable storage medium of claim 10, wherein the instructions further comprise repeating the defining and the ascertaining.

* * * * *